(12) United States Patent
Park et al.

(10) Patent No.: US 6,306,097 B1
(45) Date of Patent: Oct. 23, 2001

(54) ULTRASOUND IMAGING CATHETER GUIDING ASSEMBLY WITH CATHETER WORKING PORT

(75) Inventors: William J. Park, San Jose; Randall L. Schlesinger, San Mateo; Ricardo G. Espinosa, Milpitas, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/335,869

(22) Filed: Jun. 17, 1999

(51) Int. Cl.[7] .................................................... A61B 8/00
(52) U.S. Cl. ............................................. 600/466; 600/468
(58) Field of Search .................................. 600/459, 460, 600/466, 467, 468, 447

(56) References Cited

U.S. PATENT DOCUMENTS

| | | | |
|---|---|---|---|
| 4,794,931 | 1/1989 | Yock | 128/660.03 |
| 5,345,940 | 9/1994 | Seward et al. | 128/662.06 |
| 5,368,037 | 11/1994 | Eberle et al. | 128/662.06 |
| 5,469,853 | 11/1995 | Law et al. | 128/662.06 |
| 5,713,363 | 2/1998 | Seward et al. | 128/662.06 |
| 5,778,328 | 7/1998 | Lowe et al. | 128/662.06 |
| 5,842,994 | * 12/1998 | Tenhoff et al. | 600/466 |
| 5,879,499 | * 3/1999 | Corvi | 156/175 |
| 6,045,508 | * 4/2000 | Hossack et al. | 600/447 |

* cited by examiner

Primary Examiner—Marvin M. Lateef
Assistant Examiner—Maulin Patel
(74) Attorney, Agent, or Firm—Brinks Hofer Gilson & Lione

(57) ABSTRACT

An apparatus and method for operating a catheter guiding assembly, with one lumen providing access for an ultrasound imaging catheter and a second lumen providing a working port for a tool. Optionally, the ultrasound imaging catheter in the catheter guiding assembly is exposed to blood, and the ultrasound imaging catheter port has a gasket. Alternatively, the catheter guiding assembly is sealed to prevent blood contact by the ultrasound imaging catheter, and the ultrasound imaging catheter may be re-used several times. In either case, the working tool is in the field of view of the ultrasound imaging catheter and normally exposed to blood. Because the working tool is exposed to blood, the working port has a gasket to keep blood from leaking out. Optionally, the working port is used for fluid delivery for injecting contrast agent, chemicals or drugs, which can be activated by sonification from the ultrasound imaging catheter.

66 Claims, 5 Drawing Sheets

ULTRASOUND IMAGING CATHETER GUIDING ASSEMBLY WITH CATHETER WORKING PORT

BACKGROUND OF THE INVENTION

1. Field of Invention

This invention relates generally to diagnostic medical ultrasound imaging of a body, and more specifically to a catheter guiding assembly with a lumen for an imaging catheter and a lumen for a catheter-based working tool.

2. Description of the Prior Art

Ultrasound imaging catheters are known to the art. These ultrasound imaging catheters are single use, disposable catheters which provide a radial image inside blood vessels for medical diagnosis and an optional biopsy with an externally mounted needle or a completely separate tissue collecting tool.

U.S. Pat. No. 5,345,940 to Seward, et al. discloses an all-in-one ultrasound imaging catheter, allowing a working tool to be inserted with the ultrasound imaging catheter in one body opening. A port helps position the working tool in the field of view of the ultrasound imaging transducer in the catheter.

However, such an ultrasound imaging catheter with a port for a working tool may be too expensive to build as a disposable, one-time use catheter. And if the catheter is not disposable, catheter re-sterilization is difficult, because the port is difficult to flush for complete sterilization. Catheter re-sterilization is also difficult because of the stress re-sterilization creates for catheter materials and catheter designs. Furthermore, the prior art does not disclose a sealed port for a working tool to prevent blood leaks. Nor does the prior art disclose a sealed port for an ultrasound imaging catheter to prevent contact with blood.

Another approach involves using two separate catheters, an ultrasound imaging catheter and a catheter-based working tool. Using two separate catheters makes it more difficult to image the working tool, because the ultrasound imaging catheter needs to be maneuvered to bring the catheter-based working tool into the field of view. Once in the field of view, the working tool or the ultrasound imaging catheter can move and the working tool can leave the field of view of the ultrasound imaging catheter. The ultrasound imaging catheter would need to be continuously maneuvered and would require flexibility for steering to keep the working tool in the field of view.

A need presently exists for a catheter guiding assembly, with gaskets to seal the openings of the catheter guiding assembly, that can coordinate an ultrasound imaging catheter and a catheter-based working tool. A need also exists for sealing a reusable ultrasound imaging catheter from exposure to blood. Finally, a need exists for means to locally deliver drugs which can be activated by sonification from an ultrasound imaging catheter, and for means to locally deliver other fluids, such as chemicals or contrast agents.

SUMMARY OF THE INVENTION

An object of the present invention is to provide a catheter guiding assembly with gaskets to seal the openings of the catheter guiding assembly to prevent blood leaks.

Another object of the invention is to coordinate the operation of a catheter-based tool with the imaging of an ultrasound imaging catheter, which is optionally exposed to blood.

Another object of the invention is to provide a practical method to locally deliver drugs which can be activated by sonification from an ultrasound imaging catheter, or locally deliver other fluids, such as chemicals or contrast agents.

A first aspect of the invention is directed to a catheter guiding assembly having two lumens. A first lumen is for an ultrasound imaging catheter that can be slideably inserted. A second lumen provides a working port, and the second lumen has a gasket to prevent blood from leaking out.

A second aspect of the invention is directed to a catheter guiding assembly having two lumens. A first lumen is for an ultrasound imaging catheter that can be slideably inserted into the first lumen that is open to blood, wherein the first lumen has a gasket to prevent blood from leaking out. A second lumen provides a working port, and the second lumen has a gasket to prevent blood from leaking out.

These and other objects and advantages of the invention will become apparent to those skilled in the art from the following detailed description of the invention and the accompanying drawings.

DETAILED DESCRIPTION OF THE PREFERRED EMBODIMENTS

The invention provides a low cost method and apparatus for inserting an ultrasound imaging catheter and a working tool into a blood vessel or other structures of a human or animal body. In a preferred embodiment of the invention, the distal end of the catheter guiding assembly containing the ultrasound imaging catheter port is flexible to allow the ultrasound imaging catheter to be steerable by an operator. The ultrasound imaging catheter port can be open or closed. Preferably, prior to insertion of the ultrasound imaging catheter into a port with a closed lumen, an ultrasound coupling agent (e.g., an acoustic gel or saline solution) is applied to the lumen. The ultrasound imaging catheter may or may not come in contact with blood, depending on the particular embodiment of the invention. In an embodiment of the invention where the ultrasound imaging catheter is not in direct contact with blood, the ultrasound imaging catheter may be re-used several times. In an embodiment of the invention where the ultrasound imaging catheter is in direct contact with blood, the ultrasound imaging catheter is only used once and the ultrasound imaging catheter port has a gasket to prevent blood from leaking.

Any conmmercially available ultrasound imaging catheter can be used with the preferred embodiments of the invention. The ultrasound imaging catheter may include an ultrasound rotating single crystal transducer, or a 1-D, 1.5D, or 2-D ultrasound phased array transducer.

In a preferred embodiment, the catheter guiding assembly is an extrusion made by squeezing a plastic material through a die, and inexpensive enough for a one-time use and subsequent disposal. In the most preferred embodiment of the invention, the plastic material is Pebax® polyether block amide, available from Elf Atochem North America, located in Philadelphia, Pa. In alternative embodiments, Pellethane® thermoplastic polyurethane elastomer available from Dow Corporation, located in Midland, Mich. and Hytrel® polyester elastomer, available from Du Pont Corporation, located in Wilmington, Del. can be used. Yet other alternative embodiments of the invention could include other fabrication methods, such as molding the catheter guiding assembly in a mold, or machining the necessary features of the catheter guiding assembly from a block of suitable material. Several materials could be used for the fabrication of these alternative embodiments of the invention, such as plastic, silicone rubber, glass, ceramic, or metal.

In a preferred embodiment of the invention, the catheter-based working tool is in the field of view of the ultrasound imaging catheter. When the catheter-based working tool is exposed to blood, the working port has a gasket on the proximal end to prevent blood from leaking. In another preferred embodiment of the invention, the working port for a catheter-based working tool is used for fluid drug, chemical or contrast agent delivery. A valve (e.g., a stop-cock) may be connected (e.g., T-connected) into the working port before the gasket to provide access for injecting the fluid into the blood or for flushing the port.

Another preferred embodiment of the invention provides localized delivery of drugs for optional activation by sonification from the ultrasound imaging catheter. This would allow selective drug therapy for tissues first inspected by the ultrasound imaging catheter.

In one embodiment of the invention, the speed and placement of drug delivery are monitored by Doppler ultrasound imaging. Examples of Doppler ultrasound imaging include: Color Doppler Velocity, Color Doppler Energy, Color Doppler Variance, or any combination thereof. These modes of Doppler ultrasound imaging are disclosed in co-pending U.S. patent application Ser. No. 08/736,895, filed Oct. 25, 1996, entitled "Imaging Modality Showing Energy and Velocity," which is assigned to the assignee of the present invention and hereby incorporated by reference.

Figures 1, 2:
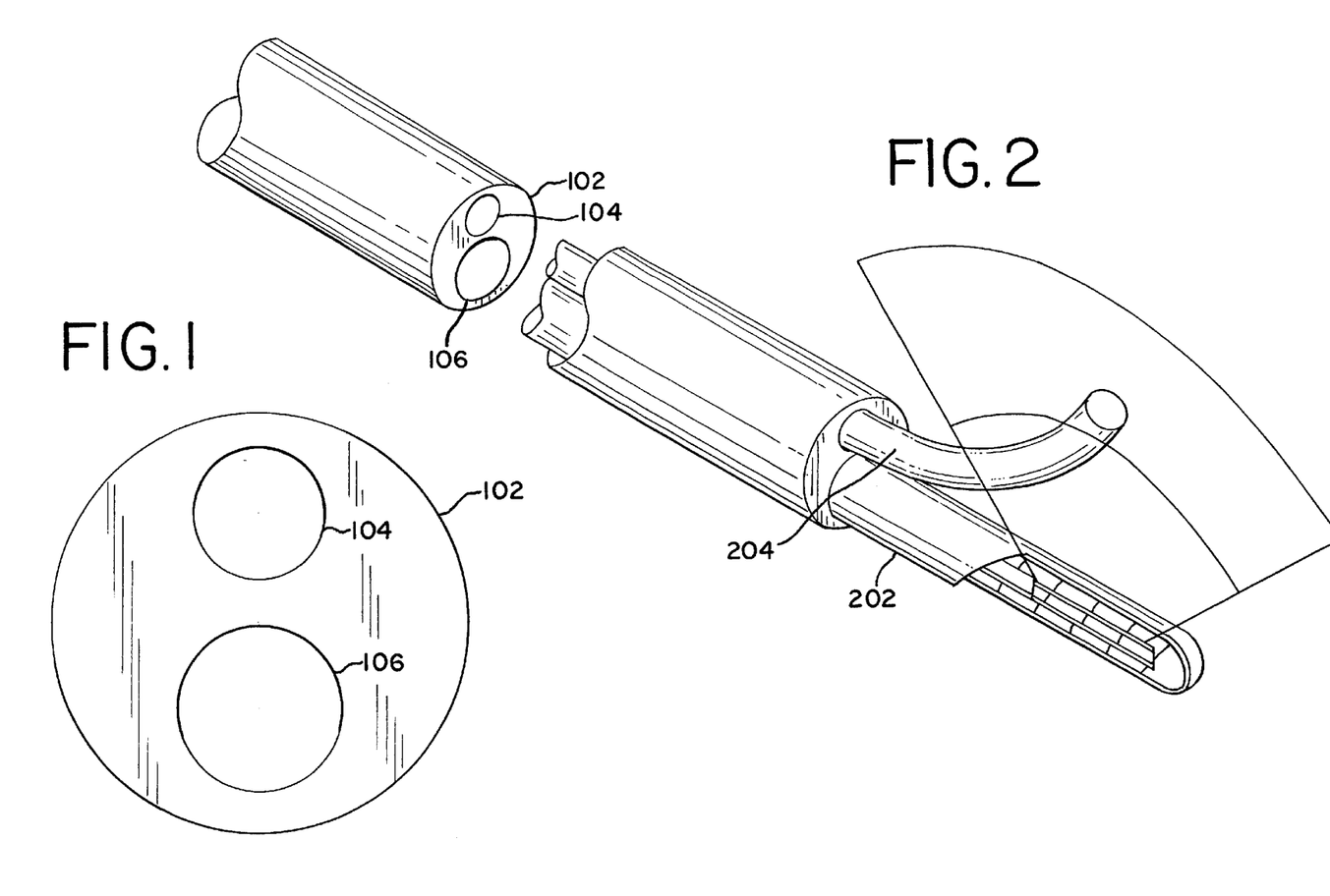
FIG. 1 shows a cross-sectional view of a preferred embodiment of the invention, which includes a main extruded shaft with two lumens.
FIG. 2 shows a perspective view of a preferred embodiment of the invention, where an extrusion extends out from the main shaft and is attached to the ultrasound lumen.

FIG. 1 shows a cross-sectional view of the invention, which includes main extruded shaft 102 with two lumens 104 and 106. Main extruded shaft 102 typically has a diameter range from 8 to 30 French and a preferred diameter range from 8 to 24 French (one French divided by three equals one millimeter). First lumen 106 (for an ultrasound imaging catheter) has a typical diameter range from 4 to 15 French and a preferred diameter range from 4 to 10 French. Second lumen 104 (for the working port) has a typical diameter range from 1 to 12 French and a preferred diameter range from 1 to 8 French. One embodiment of the invention uses main extruded shaft 102 with a material that has a high durometer hardness to keep it rigid. Main extruded shaft 102 has a typical durometer hardness range of 55 to 80 Shore D and a preferred durometer hardness of 75 Shore D. In one preferred embodiment of the invention, the durometer hardness of main extruded shaft 102 is lower than 75 Shore D to allow some bending of main extruded shaft 102.

FIG. 2 shows a perspective view of a preferred embodiment of the invention, where extended extrusion 202 extends out from main shaft 102 and is attached (e.g., thermally fused, adhesively bonded, or equivalents thereof) to ultrasound imaging catheter lumen 106. Working port extrusion 204 also extends out from main shaft 102 and is open. In the preferred embodiment of the invention, working port extrusion 204 is partially or completely in the field of view of an ultrasound imaging catheter in extended extrusion 202. Extended extrusion 202 is made of the same material as main shaft 102, but could be fabricated from a different material.

Figures 3, 4:
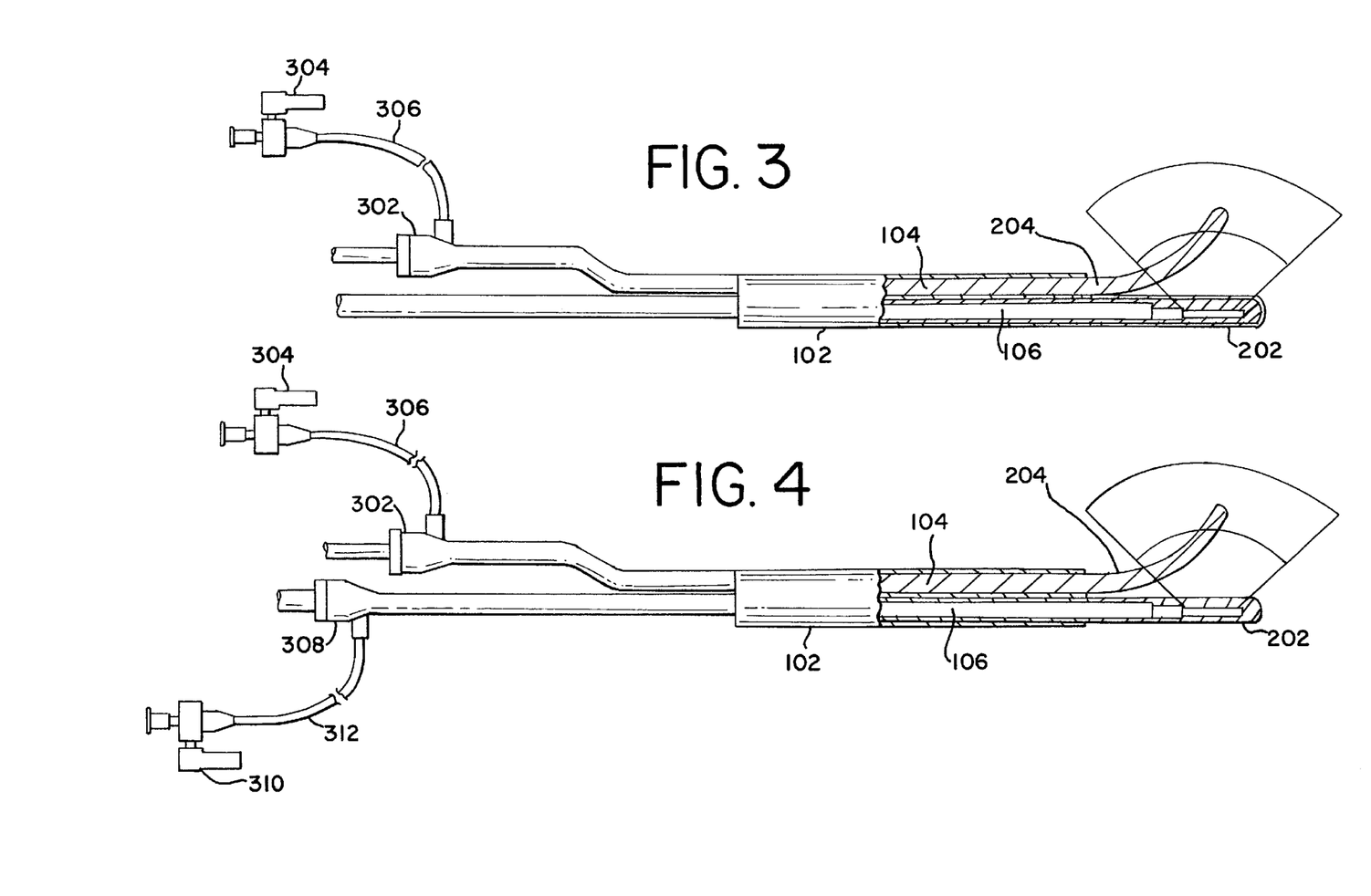
FIG. 3 shows a side view of the embodiment of the invention shown in FIG. 2.
FIG. 4 shows a side view of an alternative embodiment of the invention shown in FIG. 3.

FIG. 3 shows a side view of the embodiment of the invention shown in FIG. 2. The design of extended extrusion 202, by a proper choice of material and wall thickness, will not significantly impede ultrasound imaging. In embodiments of the invention using Pebax® polyether block amide, a typical wall thickness for extended extrusion 202 would range from 0.125 mm to 3 mm, and in preferred embodiments, the wall thickness of extended extrusion 202 would range from 0.25 mm to 0.75 mm. Extended extrusion 202 is sealed on the distal end, or in an alternative embodiment of the invention, it is open on the distal end, depending on whether the ultrasound imaging catheter is to be exposed to blood. In one embodiment of the invention, extended extrusion 202 has a low durometer hardness to allow bending when the ultrasound imaging catheter inside the extrusion is steerable. Extended extrusion 202 has a typical durometer hardness range of 25 to 55 Shore D and a preferred durometer hardness of 35 Shore D. On the opposite end of main shaft 102, there is gasket 302 on working port 104 to keep blood from pumping out. If the working port 104 is used for the delivery of fluids (e.g., drugs), stop-cock 304 is T-connected with tube 306 into working port 104 before gasket 302 and fluids (e.g., drugs, chemicals or contrast agents) are delivered through stop-cock 304.

FIG. 4 shows a side view of an alternative embodiment of the invention shown in FIG. 3. On the opposite end of main shaft 102 there is gasket 302 on working port 104 to keep blood from pumping out. As before, stop-cock 304 is T-connected with tube 306 into working port 104 before gasket 302 for the delivery of fluids (e.g., drugs, chemicals or contrast agents) through stop-cock 304. Additionally, ultrasound imaging catheter lumen 106 has extended extrusion 202 with an exposed distal end, and gasket 308 is inserted to prevent blood leaking from ultrasound imaging catheter lumen 106. An alternative embodiment of the invention has additional stop-cock 310 T-connected with tube 312 into ultrasound imaging catheter lumen 106 before gasket 308 for the delivery of fluids.

Figure 5:
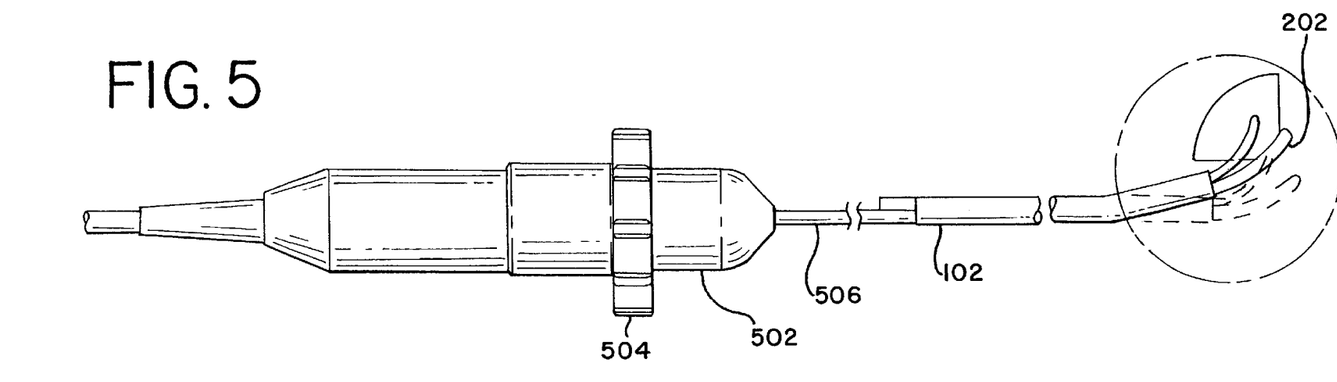
FIG. 5 shows a perspective view of a preferred embodiment of the invention, where the extrusion extends out from the main shaft and is attached to the ultrasound lumen.

FIG. 5 shows a perspective view of a preferred embodiment of the invention, where extended extrusion 202 extends out from main shaft 102 and is attached to ultrasound imaging catheter lumen 106 (not shown). Additionally, mechanical control 502 with user-operable knob 504 is attached by means of cable 506 for controlling the movement of the ultrasound imaging catheter (not shown) in extended extrusion 202.

Figure 6:
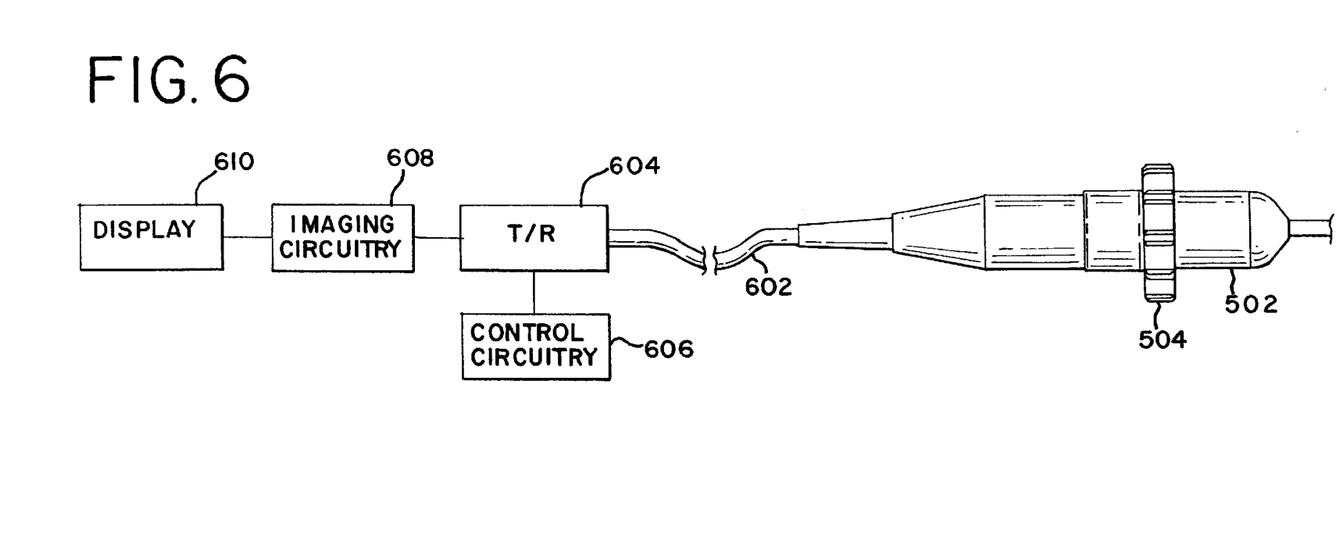
FIG. 6 shows a perspective view of a preferred embodiment of the invention, where a mechanical control with a user-operable knob is connected by cable to an ultrasound transmitter/receiver.

FIG. 6 shows a perspective view of a preferred embodiment of the invention, where mechanical control 502 with user-operable knob 504 is connected by cable 602 to ultrasound transmitter/receiver 604. Ultrasound transmitter/receiver 604 is operated by control circuitry 606 and provides signals for imaging circuitry 608 to convert into images to be shown by display 610. Optionally, there is a graphical user interface (not shown) connected to control circuitry 606 to provide the user with an easy-to-use interface to operate the invention.

Figure 7:
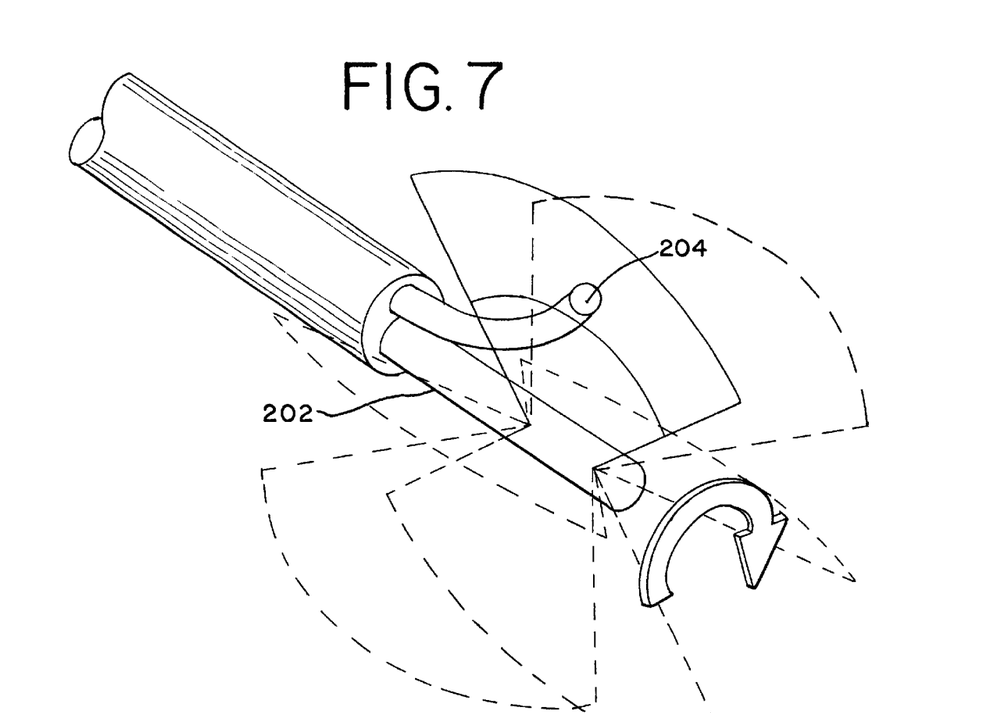
FIG. 7 is a perspective view of a preferred embodiment of the invention, showing the toroidal view of an ultrasound imaging catheter rotating inside an extrusion.

FIG. 7 is a perspective view of a preferred embodiment of the invention, showing the toroidal view of an ultrasound imaging catheter (not shown) rotating inside extended extrusion 202. In the preferred embodiment of the invention, extended extrusion 202 positions the ultrasound imaging catheter (not shown) to view the open end of working port extrusion 204 for imaging of fluid delivery or other operations. In embodiments of the invention where an ultrasound imaging catheter can rotate within a rigid catheter guiding assembly, 3-D toroidal image reconstruction possible.

Figure 8:
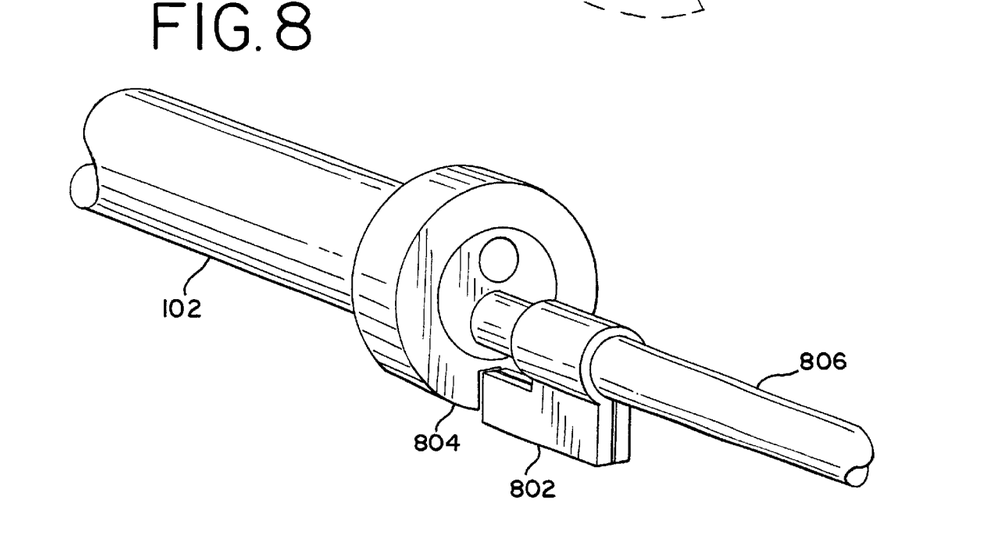
FIG. 8 is a perspective view of an alternative embodiment of the invention, showing the main extrusion and a closed ultrasound imaging catheter extrusion with a locking device to lock the orientation of an ultrasound imaging catheter.

FIG. 8 is a perspective view of an alternative embodiment of the invention, showing main shaft 102 and ultrasound imaging catheter 806. In this embodiment of the invention, extrusions 802 and 804 lock ultrasound imaging catheter 806 into a fixed orientation. One benefit of locking ultrasound imaging catheter 806 into a fixed orientation within main shaft 102 is to allow selection of the side wall characteristics of the portion of extended extrusion 202 (not shown) that is located directly over the transducer array of the ultrasound imaging catheter. The side wall characteristics of this portion of extended extrusion 202 can act as a lens (i.e., by acoustic pulse refraction) to change the imaging characteristics of the ultrasound imaging catheter 806.

Figure 9A:
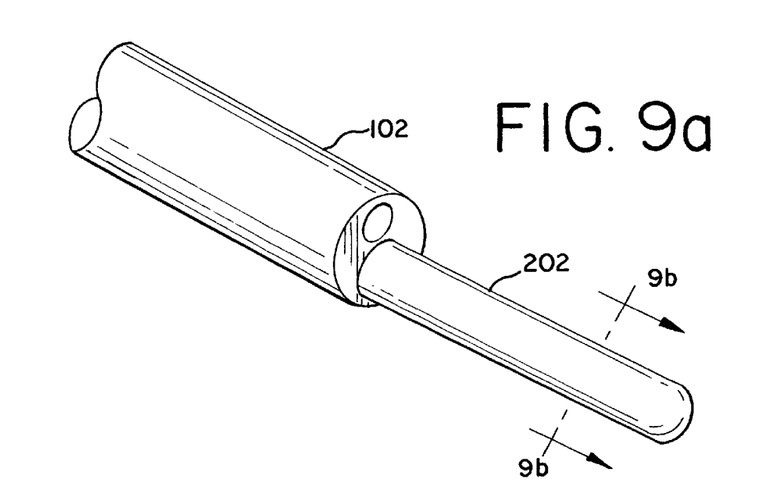
FIG. 9(a) is a perspective view of the main shaft and a closed ultrasound imaging catheter extrusion with a cross-section.
Figure 9B:
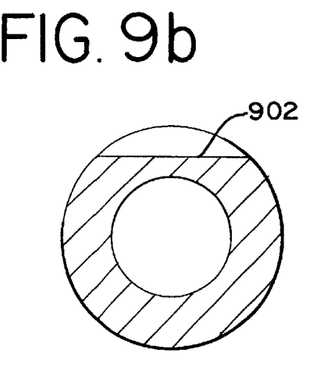
FIG. 9(b) shows a flat thin wall cross-section of the extrusion, where a segment of the cylindrical wall is removed to provide a flat external surface immediately adjacent to the array of transducers of the ultrasound imaging catheter.
Figure 9C:
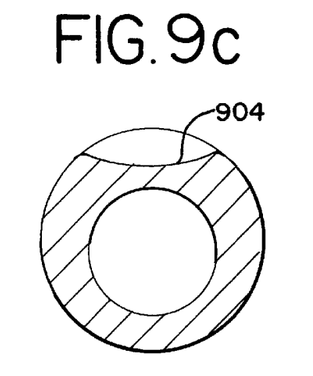
FIG. 9(c) shows a concave thin wall cross-section of the extrusion, where a segment of the cylindrical wall is removed to provide a concave external surface.
Figure 9D:
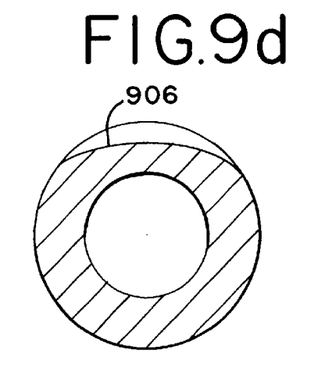
FIG. 9(d) shows a convex thin wall cross-section of the extrusion, where a segment of the cylindrical wall is removed to provide a convex external surface.
Figure 9E:
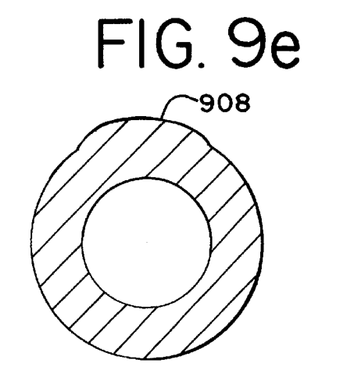
FIG. 9(e) shows a convex wall cross-section of the extrusion, where a segment of the cylindrical wall is thicker on one side to provide a convex external surface.

FIG. 9(a) is a perspective view of main shaft 102 and closed extended extrusion 202 with cross-section views taken along the line shown. In this embodiment of the invention, the ultrasound imaging catheter (not shown) is locked into a fixed orientation within the extended extrusion 202. The cross-section of extended extrusion 202 has several potential contours over the array of transducers of the ultrasound imaging catheter. FIG. 9(b) shows a flat thin wall cross-section 902 of extended extrusion 202, where a segment of the cylindrical wall is removed to provide a flat external surface immediately adjacent to the array of transducers of the ultrasound imaging catheter. FIG. 9(c) shows a concave thin wall cross-section 904 of extended extrusion 202, where a segment of the cylindrical wall is removed to provide a concave external surface immediately adjacent to the array of transducers of the ultrasound imaging catheter. FIG. 9(d) shows a convex thin wall cross-section 906 of extended extrusion 202, where a segment of the cylindrical wall is removed to provide a convex external surface immediately adjacent to the array of transducers of the ultrasound imaging catheter. FIG. 9(e) shows a convex wall cross-section 908 of extended extrusion 202, where a segment of the cylindrical wall is thicker on one side to provide a convex external surface immediately adjacent to the array of transducers of the ultrasound imaging catheter.

These contours can be designed to have no effect on the propagation of an acoustic beam, or alternatively, they can be designed to focus or de-focus the propagation of an acoustic beam. The material used to fabricate extended extrusion 202 will determine the effect that the contour has on the focusing/de-focusing of the acoustic beam.

In general, a material with an acoustic beam propagation velocity greater than the acoustic beam propagation velocity in soft tissue will focus an acoustic beam, if the material thickness at the center of the contour is less than at the edges. The amount of focusing will vary as the delta between the center and edge thickness varies and as the shape of the contour varies. This is the case for the contours shown in FIGS. 9(b), 9(c), and 9(d), for a preferred embodiment using Pebax®, which has an acoustic beam propagation velocity of 1565 meters/second (m/sec), which is slightly greater than the acoustic beam propagation velocity of 1540 m/sec in soft tissue. Therefore, the contour shown in FIG. 9(c) will focus an acoustic beam more than the contour shown in FIG. 9(b), and the contour shown in FIG. 9(b) will focus an acoustic beam more than the contour shown in FIG. 9(d). For the same material, which has an acoustic beam propagation velocity greater than the acoustic beam propagation velocity in soft tissue, a contour with a thicker center than the edges will have a de-focusing effect on the acoustic beam. Therefore, if Pebax® is used to fabricate the extended extrusion 202, a contour with a thicker center than the edges (shown in FIG. 9(e)) will have a de-focusing effect on the acoustic beam.

In general, a material with an acoustic beam propagation velocity less than the acoustic beam propagation velocity in soft tissue will de-focus an acoustic beam, if the material thickness at the center of the contour is less than at the edges. The amount of de-focusing will vary as the delta between the center and edge thickness varies and as the shape of the contour varies. If room temperature vulcanizing silicone rubber (RTV), which has an acoustic beam propagation velocity of 970 m/sec, is used to fabricate the extended extrusion 202, the result for the case of the contours shown in FIGS. 9(b), 9(c), and 9(d) will be to de-focus the acoustic beam. For the same material, which has an acoustic beam propagation velocity less than the acoustic beam propagation velocity in soft tissue, a contour with a thicker center than the edges will have a focusing effect on the acoustic beam. Therefore, if RTV were is to fabricate the extended extrusion 202, a contour with a thicker center than the edges (shown in FIG. 9(e)) will have a focusing effect on the acoustic beam.

An alternative embodiment of the invention can be fabricated by mechanically or chemically attaching two tubes together, to provide a port for a working tool and a port for an ultrasound imaging catheter. This embodiment of the invention is potentially easier to implement and thus lower in cost. The tubes can be fabricated from the same material or from different materials. Such tubes can also be interchangeable, depending on the desired application of the catheter guiding assembly.

The preferred embodiments of the invention with one or more gaskets extend the application of ultrasound imaging catheters with working tools into areas of the heart and other vessels of the body where blood pressure can result in leaks from the catheters. Such working tools include radio frequency (RF) ablation devices, tissue cutting tools, tissue freezing tools, biopsy tools, and various tools for blood vessel or artery modification (e.g., balloons or devices to change the inner diameter of a blood vessel or artery). The procedures for using the preferred embodiments of the invention for operating a working tool guided by an ultrasound imaging catheter are all quite similar, as illustrated by the two following examples.

One example of a procedure for using a RF ablation device starts with the insertion of an ultrasound imaging catheter into the imaging catheter lumen of the catheter guiding assembly. Then the catheter guiding assembly is inserted into a human or animal body in the desired location. Then a RF ablation device is inserted into the working port of the catheter guiding assembly. The ultrasound imaging catheter is used to visually guide the placement of the RF ablation device in the desired target location. The RF ablation is performed, and the RF ablation device is removed from the catheter guiding assembly. Then the catheter guiding assembly is removed from the human or animal body.

One example of a procedure for using a biopsy device starts with the insertion of an ultrasound imaging catheter into the imaging catheter lumen of the catheter guiding assembly. Then the catheter guiding assembly is inserted into a human or animal body in the desired location. Then a biopsy device is inserted into the working port of the catheter guiding assembly. The ultrasound imaging catheter is used to visually guide the placement of the biopsy device in the desired target location. The biopsy is performed, and the biopsy device is removed from the catheter guiding assembly. Then the catheter guiding assembly is removed from the human or animal body.

The exemplary embodiments described herein are for purposes of illustration and are not intended to be limiting. For example, a catheter guiding assembly with two or more working ports would be an alternative embodiment of the invention. As another example, a catheter guiding assembly with two of more ultrasound imaging catheter lumens would be an alternative embodiment of the invention. As another example, the use of a valve other than a stop-cock for controlling the delivery of fluids would be an alternative embodiment of the invention. As another example, the use of an electronic user control would be an alternative embodiment of the invention. As another example, the use of a gasket easily penetrated by a working tool, such as a thin gasket, or the use of a sufficiently viscous putty as a gasket, would be an alternative embodiment of the invention. As another example, one or more gaskets placed in the distal end of a lumen or anywhere between the distal end and the proximal end of the lumen would be an alternative embodiment of the invention. As another example, a catheter guiding assembly with interchangeable components would be an alternative embodiment of the invention. Therefore, those skilled in the art will recognize that other embodiments could be practiced without departing from the scope and spirit of the claims set forth below.

What is claimed is:

1. A catheter guiding assembly, comprising:

a shaft having a first lumen and a second lumen, extending substantially lengthwise through the shaft;

the first lumen having a distal end and an open proximal end for insertion of an ultrasound imaging catheter; and the second lumen providing a working port, having an open distal end and a proximal end, with a gasket in the second lumen.

2. The catheter guiding assembly of claim 1, further comprising an ultrasound imaging catheter having a steerable distal tip.

3. The catheter guiding assembly of claim 2, wherein the steerable distal tip of the ultrasound imaging catheter is controllable by an operator control disposed at the proximal end.

4. The catheter guiding assembly of claim 3, wherein the operator control is electronic.

5. The catheter guiding assembly of claim 1, wherein the catheter guiding assembly has a proximal end, a main body and a distal end, in which the distal end is flexible.

6. The catheter guiding assembly of claim 1, further comprising an ultrasound imaging catheter having a distal end, a main body and a proximal end, and the ultrasound imaging catheter imaging is controllable by a user control disposed at the proximal end.

7. The catheter guiding assembly of claim 1, wherein the catheter guiding assembly has a proximal end, a main body and a distal end, in which the distal end of the first lumen is flexible and allows for the movement of an ultrasound imaging catheter having steerable distal tip capabilities.

8. The catheter guiding assembly of claim 1, further comprising an ultrasound imaging catheter such that the second lumen lies within the plane of the field of view of the ultrasound imaging catheter in the first lumen.

9. The catheter guiding assembly of claim 1, further comprising means for controlling the transfer of a fluid through the second lumen.

10. The catheter guiding assembly of claim 1, further comprising a valve connected to the proximal end of the second lumen.

11. The catheter guiding assembly of claim 1, further comprising a stop-cock T-connected to the proximal end of the second lumen for controlling the delivery of a fluid through the second lumen.

12. The catheter guiding assembly of claim 1, wherein the first lumen allows an ultrasound imaging catheter to be rotated to gather a plurality of planes of view to create a toroidal 3-D image.

13. The catheter guiding assembly of claim 1, wherein the second lumen has a working port that allows a catheter-based tool to be rotated or manipulated.

14. The catheter guiding assembly of claim 1, wherein the second lumen has a working port which maintains a catheter-based tool in a fixed orientation relative to an ultrasound imaging catheter in the first lumen.

15. The catheter guiding assembly of claim 1, wherein the ultrasound imaging catheter is fixed in orientation in the first lumen.

16. The catheter guiding assembly of claim 1, wherein the catheter guiding assembly has a shaft diameter of 8 to 30 French.

17. The catheter guiding assembly of claim 1, wherein the catheter guiding assembly has a shaft diameter of 8 to 24 French.

18. The catheter guiding assembly of claim 1, wherein the first lumen has a diameter of 4 to 15 French.

19. The catheter guiding assembly of claim 1, wherein the first lumen has a diameter of 4 to 10 French.

20. The catheter guiding assembly of claim 1, wherein the second lumen has a diameter of 1 to 12 French.

21. The catheter guiding assembly of claim 1, wherein the second lumen has a diameter of 1 to 8 French.

22. The catheter guiding assembly of claim 1, wherein the catheter guiding assembly is comprised of a material having a durometer hardness range of 55 to 80 Shore D.

23. The catheter guiding assembly of claim 1, wherein the catheter guiding assembly is comprised of a material having a durometer hardness of 75 Shore D.

24. The catheter guiding assembly of claim 1, wherein the catheter guiding assembly is comprised of a material having a durometer hardness less than 75 Shore D.

25. The catheter guiding assembly of claim 1, wherein the catheter guiding assembly has a proximal end, a main body and a distal end, in which the distal end comprises an extended extruded shaft of a material having a durometer hardness range of 25 to 55 Shore D.

26. The catheter guiding assembly of claim 1, wherein the catheter guiding assembly has a proximal end, a main body and a distal end, in which the distal end comprises an extended extruded shaft of a material having a durometer hardness of 35 Shore D.

27. The catheter guiding assembly of claim 1, further comprising an ultrasound imaging catheter including an ultrasound rotating single crystal transducer.

28. The catheter guiding assembly of claim 1, further comprising an ultrasound imaging catheter including an ultrasound phased array transducer.

29. The catheter guiding assembly of claim 1, further comprising an ultrasound imaging catheter including an ultrasound phased array transducer for Doppler imaging.

30. The catheter guiding assembly of claim 1, wherein the distal end of the first lumen is closed.

31. The catheter guiding assembly of claim 28, wherein the distal end of the first lumen is composed of a material which focuses ultrasound transmitted by the ultrasound phased array transducer of the ultrasound imaging catheter.

32. The catheter guiding assembly of claim 28, wherein the distal end of the first lumen is composed of a material with a side wall shaped to not focus ultrasound transmitted by the ultrasound phased array transducer of the ultrasound imaging catheter.

33. The catheter guiding assembly of claim 28, wherein the distal end of the first lumen is composed of a material with a side wall shaped to de-focus ultrasound transmitted by the ultrasound phased array transducer of the ultrasound imaging catheter.

34. The catheter guiding assembly of claim 28, wherein the distal end of the first lumen is thinner in a portion of the side wall of the distal end to focus acoustic beams transmitted by an ultrasound imaging catheter.

35. A catheter guiding assembly, comprising:
   a shaft having a first lumen and a second lumen, extending substantially lengthwise through the shaft;
   the first lumen including a distal end and an open proximal end for insertion of an ultrasound imaging catheter, wherein the distal end of the first lumen is open and the proximal end of the first lumen has a gasket; and
   the second lumen providing a working port, including an open distal end and a proximal end, with a gasket in the second lumen.

36. The catheter guiding assembly of claim 35, further comprising an ultrasound imaging catheter having a steerable distal tip.

37. The catheter guiding assembly of claim 35, further comprising an ultrasound imaging catheter, wherein the steerable distal tip of the imaging catheter is controllable by an operator control disposed at the proximal end.

38. The catheter guiding assembly of claim 37, wherein the operator control is electronic.

39. The catheter guiding assembly of claim 35, wherein the catheter guiding assembly has a proximal end, a main body and a distal end, in which the distal end is flexible.

40. The catheter guiding assembly of claim 35, further comprising an ultrasound imaging catheter having a distal end, a main body and a proximal end, and the ultrasound imaging catheter imaging is controllable by a user control disposed at the proximal end.

41. The catheter guiding assembly of claim 35, wherein the catheter guiding assembly has a proximal end, a main body and a distal end, in which the distal end of the first lumen is flexible and allows for the movement of an imaging catheter with steerable distal tip capabilities.

42. The catheter guiding assembly of claim 35, further comprising an ultrasound imaging catheter such that the second lumen lies within the plane of the field of view of the ultrasound imaging catheter in the first lumen.

43. The catheter guiding assembly of claim 35, further comprising means for controlling the transfer of a fluid through the second lumen.

44. The catheter guiding assembly of claim 35, further comprising an ultrasound imaging catheter including an ultrasound phased array transducer capable for Doppler imaging.

45. The catheter guiding assembly of claim 35, further comprising a valve connected to the proximal end of the second lumen.

46. The catheter guiding assembly of claim 35, further comprising a stop-cock T-connected to the proximal end of the second lumen for controlling the delivery of a fluid through the second lumen.

47. The catheter guiding assembly of claim 35, wherein the first lumen allows an ultrasound imaging catheter to be rotated to gather planes of views to create a toroidal 3-D image.

48. The catheter guiding assembly of claim 35, wherein the second lumen has a working port which allows a catheter-based tool to be rotated or manipulated.

49. The catheter guiding assembly of claim 35, wherein the second lumen has a working port which maintains a catheter-based tool in a fixed orientation relative to an ultrasound imaging catheter in the first lumen.

50. The catheter guiding assembly of claim 35, further comprising an ultrasound imaging catheter fixed in orientation in the first lumen.

51. The catheter guiding assembly of claim 35, wherein the catheter guiding assembly has a shaft diameter of 8 to 30 French.

52. The catheter guiding assembly of claim 35, wherein the catheter guiding assembly has a shaft diameter of 8 to 24 French.

53. The catheter guiding assembly of claim 35, wherein the first lumen has a diameter of 4 to 15 French.

54. The catheter guiding assembly of claim 35, wherein the first lumen has a diameter of 4 to 10 French.

55. The catheter guiding assembly of claim 35, wherein the second lumen has a diameter of 1 to 12 French.

56. The catheter guiding assembly of claim 35, wherein the second lumen has a diameter of 1 to 8 French.

57. The catheter guiding assembly of claim 35, wherein the catheter guiding assembly is comprised of a material having a durometer hardness range of 55 to 80 Shore D.

58. The catheter guiding assembly of claim 35, wherein the catheter guiding assembly is comprised of a material having a durometer hardness of 75 Shore D.

59. The catheter guiding assembly of claim 35, wherein the catheter guiding assembly is comprised of a material having a durometer hardness less than 75 Shore D.

60. The catheter guiding assembly of claim 35, wherein the catheter guiding assembly has a proximal end, a main body and a distal end, in which the distal end comprises a material having a durometer hardness range of 25 to 55 Shore D.

61. The catheter guiding assembly of claim 35, wherein the catheter guiding assembly has a proximal end, a main body and a distal end, in which the distal end comprises a material having a durometer hardness of 35 Shore D.

62. The catheter guiding assembly of claim 35, further comprising an ultrasound imaging catheter including an ultrasound rotating single crystal transducer.

63. The catheter guiding assembly of claim 35, further comprising an ultrasound imaging catheter including an ultrasound phased array transducer within the catheter.

64. The catheter guiding assembly of claim 63, wherein the ultrasound imaging catheter includes an ultrasound phased array transducer capable of Doppler imaging.

65. The catheter guiding assembly of claim 35, further comprising a valve connected to the proximal end of the first lumen.

66. The catheter guiding assembly of claim 65, further comprising a stop-cock T-connected to the proximal end of the first lumen for controlling the delivery of a fluid through the first lumen.

* * * * *